US005583008A

United States Patent [19]
Johnson et al.

[11] Patent Number: 5,583,008
[45] Date of Patent: Dec. 10, 1996

[54] RAPID DIAGNOSTIC PROCEDURE FOR IVERMECTIN RESISTANCE

[75] Inventors: Carl D. Johnson, Black Earth, Wis.; Warwick N. Grant; Peter Hunt, both of Armidale, Australia

[73] Assignee: NemaPharm, Inc., Cambridge, Mass.

[21] Appl. No.: 71,251

[22] Filed: May 19, 1993

[51] Int. Cl.$^6$ ........................................ C12Q 1/02
[52] U.S. Cl. ........................................ 435/29
[58] Field of Search ........................... 435/29, 243, 245, 435/968; 424/405; 514/30; 436/172

[56] References Cited

U.S. PATENT DOCUMENTS

| | | | |
|---|---|---|---|
| 5,124,358 | 6/1992 | Kapil | 514/603 |
| 5,139,948 | 8/1992 | Shoop | 435/244 |
| 5,189,026 | 2/1993 | Costa | 514/30 |
| 5,192,546 | 3/1993 | Abercrombie | 424/405 |

OTHER PUBLICATIONS

Day, C. H. et al., The Genetics of Ivermectin–Resistant Mutants, *Abstract of International C. elegans Meeting*, p. 62 (1989).

Hedgecock, E. M. et al., Axonal Guidance Mutants of *Caenorhabditis elegans* Identified by Filling Sensory Neurons with Fluorescein Dyes, *Develop. Biol.* 111:158–170.

Hedgecock, E. M., Staining Sensory Neurons with Carbocyanine Dyes, *Worm Breeder's Gazette* 1:56 (1989).

Hunt, P. et al., Amphid Function, Chemotaxis and Ivermectin Resistance, *Abstract of International C. elegans Meeting*, p. 206 (1993).

Johnson, C. D. et al., Ivermectin Resistance in Free–Living Nematodes, *Abstracts of International C. elegans Meeting*, p. 224 (1993).

Johnson, C. D. et al., The Isolation of Mutants Resistant to the Avermectins, *Abstracts of International C. elegans Meeting*, p. 189 (1989).

Kim et al, Ivermectin Resistance in *C. elegans*, *Abstracts of International C. elegans Meeting*, p. 184 (1991).

Prichard, R. K., Anthelmintic Resistance in Nematodes: Extent, Recent Understanding and Future Directions for Control and Research, *Int. J. Parasitol.* 20:515–523 (1990).

Shoop, W. L., Ivermectin Resistance, *Parasitology Today* 9:154–159 (1993).

*Primary Examiner*—Ralph J. Gitomer
*Attorney, Agent, or Firm*—Sterne, Kessler, Goldstein & Fox P.L.L.C.

[57] ABSTRACT

The invention is directed to a rapid, efficient, inexpensive screening and diagnostic procedure for detecting avermectin/milbemycin resistance in parasitic nematodes. The procedure is designed for field use. The method entails the incubation of nematode sensillum with specific visible or fluorescent dyes that intercalate and diffuse in membranes of sensory neurons on the outer surface of wild-type nematodes but which do not bind or have reduced binding in resistant nematodes. The method is particularly directed to ivermectin resistant parasitic nematodes.

10 Claims, No Drawings

RAPID DIAGNOSTIC PROCEDURE FOR IVERMECTIN RESISTANCE

BACKGROUND OF THE INVENTION

1. Field of the Invention

The invention relates to a method for inexpensive and rapid screening of resistance to avermectins and milbemycins in parasitic nematodes. The method generally relates to the diagnosis of resistance by analysis of defects in the membranes of the sensory neurons in the chemosensory apparatus (sensillum) of nematodes. The method specifically relates to the diagnosis of resistance by the use of lipophilic dyes that stain sensory neurons in the chemosensory apparatus (sensillum) in wild-type nematodes but do not stain the sensory nematodes or have a reduced level of staining in the resistant nematodes.

2. Description of the Background Information

A. The Nematode *Caenorhabditis elegans*

The free-living soil nematode *Caenorhabditis elegans* is a simple invertebrate animal which is small (adults of both sexes, hermaphrodites and males, are approximately 1 mm long) and easily cultured in the laboratory. Methods for growing *C. elegans* are well-known to those skilled in the art. Brenner, S., *Genetics* 77:71–94 (1974); "The Nematode *Caenorhabditis elegans*," W. B. Wood, ed., 1988, Cold Spring Harbor Laboratory. For example, *C. elegans* can be grown either on agar surfaces seeded with *Escherichia coli* bacteria as a food source or in liquid cultures containing *E. coli*. Under optimal conditions eggs develop into egg-laying adults in less than three days; unmated hermaphrodites produce approximately 300 progeny. Thus it is easy to produce large numbers of animals and assays utilizing nematodes can be performed rapidly and in small volumes. These advantages have been noted by others who have used *C. elegans* as a test organism for anthelmintic and nematocide evaluation. Ohba, K. et al., *J. Pestic. Sci* 9:91–96 (1984); Vanfleteren, J. R. et al., *Nematologica* 18:325 (1972); Platzer, E. G. et al., *J. Nematol.* 9:280 (1977); Simpkin, K. G. et al., *J. Chem. Tech. Biotechnol.* 31:66 (1981); Spence, A. M. et al., *Can. J. Zool.* 60:2616 (1982); Popham, J. D. et al., *Environ. Res.* 20:183 (1979).

Over the last 15 years, the biology of *C. elegans* has been the subject of an intense scientific research effort. As a result, this organism is now genetically and biologically the best understood metazoan species. Wood, supra; Kenyon, C., *Science* 240:1448–1453 (1988). Methods for the generation, isolation, and analysis of single gene mutations have been developed and are facilitated by the rapid growth and ease of culture noted above as well as by ability of hermaphrodites to reproduce by self-fertilization.

Many mutant nematode strains have been described which display specific, characteristic responses to different classes of chemical agents. For example, Brenner, S., *Genetics* 77:71–94 (1974), among others (review Rand, J. B. et al., *Psychopharm. Bull.* 21:623–630 (1985)), discloses a series of mutants of *C. elegans* which are resistant to the cholinesterase inhibitors aldicarb, lannate or trichlorfon. Rand et al., supra, note that mutants resistant to one of these compounds are resistant to all three.

Brenner, supra, as well as Lewis, J. A. et al., *Neurosci.* 5:967–989 (1980), and Lewis, J. A. et al., *Genetics* 95:905–928 (1980), disclose the construction of a series of mutants resistant to the anthelmintic levamisole. The authors identify three classes of mutants based upon phenotypic analysis. The authors state that the most resistant class of mutants might lack one class of pharmacologically functional acetylcholine receptors.

Tabuse, Y. et al., *Carcinogenesis* 4:783–786 (1983), discloses the construction of a set of nematode mutants which are resistant to the mammalian tumor promoter 12-O-tetradecanoylphorbol-13-acetate (TPA).

In addition to mutants directed against membrane localized events, many mutants with intracellular targets have been described. For example, Sanford, T. et at., *J. Biol. Chem.* 258:12804–12809 (1983), discloses the isolation of mutants which are resistant to the RNA polymerase II inhibitor, α-amanitin. The authors discuss the use of these mutants to identify structural genes encoding subunits of RNA polymerase or its effectors.

Nematodes have been shown to respond to a variety of bioactive compounds in the same chemical form as that to which the higher vertebrates respond. For example, Morgan, P. G. et al., *Anesthesiology* 62:738–744 (1985), discloses the identification of a series of mutants which respond characteristically to volatile anesthetics. The mutants are characterized through their phenotypic expression in response to induction of anesthesia.

Trent, C. et al., *Genetics* 104:619–647 (1983), discloses the construction of mutants that are defective in egg-laying. The authors define four distinct categories of mutants based on their responses to the pharmacological agents serotonin and imipramine.

To date, over 700 genes have been identified by mutations. Wood, supra, pp. 502–559. Stable strains carrying these mutations are easily maintained either on agar plates or, for long term storage, frozen in liquid nitrogen.

Thus, the nematode *C. elegans* provides a versatile, non-vertebrate, in vivo animal model of the higher eukaryotes, which is economical to maintain, technically simple to utilize, amenable to genetic manipulation, and inherently responsive to bioactive agents which modulate pharmacological and biochemical activities in the higher vertebrates and, especially, in man.

B. Ivermectin Resistance

The avermectins/milbemycins represent a class of broad spectrum anthelmintics that share cross-resistance. Related bacterial species produce these two classes of compounds. Hundreds of synthetic related compounds have been synthesized.

Avermectins are a relatively new class of anti-nematode and anti-arthropod compound with high potency and comparatively low mammalian toxicity. Avermectins are used extensively for the control of nematode parasites in animals, including humans. The commercially available avermectins are produced by minor chemical modifications of fermentation products isolated from soil bacteria of the genus Streptomyces. Currently, the most significant commercial product is 22,23 dihydroavermectin $B_1$, also known as ivermectin and marketed as IVOMEC. Ivermectin can be obtained from country feed stores or veterinary supply houses.

Ivermectin, a member of the avermectin/milbemycin class of parasiticides, is a broad spectrum endectocide that has been safely used in several mammalian species including man. Over 60 countries have approved the use of this drug for controlling parasites in humans, cattle, sheep, horses, goats, pigs, dogs, or other mammals. (Campbell, W. C. et al., *Science* 221:823–828 (1983); Di Netta, J., in *Ivermectin and Abamectin* (Campbell, W. C., ed.), pp. 344–346, Springer-Verlag (1989).)

Other classes of broad spectrum anthelmintics have declined in usefulness as a result of the development of resistance by the parasites against which they have been used. The development of resistance to pesticidal and parasiticidal agents is a problem in the field. During the development of drug resistance, there is a change in the gene frequency of a population as a result of drug selection. Susceptible members of the population are removed by the toxic drug, while the resistant members then are allowed to expand into the parasitic population. Increased amounts of the drug are required to produce the same effect. However, organisms resistant to higher concentrations of the drug then consequently expand into the parasitic population. This is a problem to be expected when a drug is applied repeatedly and in high concentrations to a parasitic population.

The use level (the level at which the pesticide or parasiticide is applied) may differ from the actual level initially effective to kill the parasite. Consequently, resistance to low levels of the pesticide may have developed long before the resistance to the high levels is evident. The development of ivermectin resistance in the field is characterized by a failure to detect the early low-level development of resistance because ivermectin use is often repeated and intensive. The detection of resistance to ivermectin or other pestcontrolling agents while the proportion of resistant genotypes is still small, is essential to the control of resistance. Resistance to anti-nematode compounds (anthelmintics) in common use has been observed, generally too late for intervention. (Anthelmintic resistance in nematodes: extent, recent understanding, and future directions for control and research, Pritchard, R. K., *Ent. J. Parisitol.* 20:515–523 (1990).) Resistance to ivermectin, the most recently introduced and most potent anthelmintic, is an emerging problem and, accordingly, a diagnostic for ivermectin resistance is urgently needed.

The presence of an ivermectin-resistant organism was reported in South Africa 33 months after the drug was introduced and used on sheep. (Carmichael, I. et al., *J. South African Vet. Assoc.* 58:93 (1987).) In addition, there have been other field reports of ivermectin-resistant isolates of *H. contortus* from sheep in South Africa (van Wyk, J. A. et al., *Vet. Rec.* 123:226–228 (1988)), and reports of five other isolates suspected of resistance (van Wyk, J. A. et al., *Onderstepoort J. Vet. Res.* 56:41–49 (1989). In all of these reports, high use levels failed to produce efficiency of protection. Resistance to ivermectin was also reported in an *H. contortus* isolate from sheep in Brazil (Echevarria, F. A. M. et al., *Vet. Rec.* 124:147–148 (1989)). Four reports of ivermectin-resistant Otrifurcata from goats were reported from New Zealand (Watson, T. C. et al., *N. Z. Vet. J.* 38:50–53 (1990); Badger, S. B. et at., *N. Z. Vet. J.* 38:72–74 (1990); McKenna, P. B. et al., *N. Z. Vet. J.* 38:114, 117 (1990); Pomonoy, W. E. et al., *N. Z. Vet. J.* 40:76–78 (1992)). Ivermectin resistance was also discovered in the United States in a goat population infected with *H. contortus* (Craig, T. M. et at., *Vet. Rec.* 126:580 (1990)). Ivermectin resistance was also reported in Europe in a goat strain of Ostertagia spp. from Scotland (Jackson, F. et al., *Res. Vet. Sci.* 53:371–374 (1992); Jackson, F. et al., *Vet Rec.* 130:210–211 (1992)).

Tests for ivermectin resistance have required necroscopy or fecal egg count reduction (herein "FECR"). Further, the manufacturer's recommended use level has been employed as the threshold of resistance in these tests. The sensitivity of FECR tests for detecting ivermectin resistance at low frequencies is unknown. Reliance upon necroscopy following treatment is impractical as a routine procedure to monitor resistance. Accordingly, an in vitro diagnostic which is easily interpretable, inexpensive, and capable of detecting ivermectin resistance at frequencies below the manufacturer's recommended use level are needed. (Shoop, W. L., *Parasitology Today* 9:154–159 (1993)).

In vitro tests for detecting ivermectin resistance have been reported, although none of these tests are routinely used. All show resistance to use levels of ivermectin, and it is unclear whether low-level ivermectin resistance could be detected by these tests. The first test is a larval development test in vitro in which *T. colubriformis* eggs are incubated in the presence of various concentrations of ivermectin and the proportions of live larvae at various larval stages are compared (Giodano, D. J. et al., *Vet. Parasitol.* 30:139–148 (1988)). A second test is based on the in vitro development from the $L_1$ to $L_3$ larval stages of *H. contortus* (Taylor, M. A., *Res. Vet. Sci.* 49:198–202 (1990)). A third in vitro test assays development from the egg to the larval stage $L_3$ of *H. contortus* (Lacy, E. et al., in *Resistance of Parasites to Antiparasitic Drugs* (Boray, J. C. et al., eds.), pp. 177–184, MSD AGVET Merck & Co. (1990); Hubert, J. et al., *Vet. Rec.* 130:442–446 (1992)). A fifth in vitro test examines larval motility of the $L_3$ larval stage of *H. contortus* (Gill, G. H. et al., *Int. J. Parasitol.* 21:771–776 (1991)). Isoenzyme analysis has also been used to distinguish ivermectin resistant and susceptible strains (Echevarria, F. A. M. et al., *Vet. Parasitol.* 44:87–95 (1992)). Obviously, these types of tests are not amenable to rapid and inexpensive field testing.

Ivermectin resistance has been observed only in Trichostrongylus from the gastrointestinal tract of sheep and goats. However, the possibility of resistance in other worms has been raised. Ivermectin is currently used as a treatment for humans infected with *O. volvulus*. The main goal of this therapy is to eliminate the microfilariae. This use was suggested by the activity of ivermectin against microfilariae of *D. immitis* in dogs, *O. cervicalis* in horses, and *O. gibsoni* in cattle (Egerton, J. H. et al., *Br. Vet. J.* 136:88–97 (1980); Blair, L. S. et al., *Am J. Vet. Res.* 44:475–477 (1983); Klei, T. R., et al., *J. Parasitol* 66:859–861 (1980); Egerton, J. R. et al., *Vet. Parasitol* 8:83–88 (1981); Forsyth, K. P. et al., *Exp. Parasitol* 58::41–55 (1984)).

Ivermectin resistance has been analyzed in the model nematode *C. elegans* by isolating ivermectin-resistant mutants (Johnson, C. D. et al., *Abstracts of Int. C. Elegans Meet.*, p. 189 (1989); Day, C. H. et al., *Abstracts of Int. C. Elegans Meet.*, p. 62 (1989); Kim et al., *Abstracts Int. C. Elegans Meet.*, p. 184 (1989)). The results of these analyses have shown the following. A single mutation confers low-level resistance (5 or 10 ng/ml) in one of 23 avr genes distributed over five chromosomes. High-level resistance (20–25,000 ng/ml) is conferred by single recessive mutations of defined avr genes, dominant mutations, or two mutations in new avr genes. Most of the resistance at high levels of ivermectin requires mutations in two genes. The vast majority of ivermectin-resistant mutants are resistant to low levels of ivermectin. The significance of these studies is that the prevalent resistance observed in parasites will probably be low-level resistance. Ivermectin resistance observed in parasitic nematodes (Shoop, W. L., supra) shows that the level of resistance is similar to that observed in low-level ivermectin-resistant strains of *C. elegans*. This result could be predicted from the *C. elegans* experiments discussed above.

SUMMARY OF THE INVENTION

The invention is based on the inventors' following discoveries and their consideration that the following discoveries have a valuable diagnostic application.

1. Low-level resistance in four non-*C. elegans* species of free-living nematodes occurs at frequencies similar to those observed in *C. elegans*.

2. Some mutations that confer defects in chemosensory function, and had previously been identified as mutations of che, osm, or daf genes, also confer low-level ivermectin resistance. Of particular significance, there is a positive correlation between the che, osm, or daf mutations that confer ivermectin resistance and those mutations that have previously been reported to lack the staining of sensory neurons (whose membranes are normally exposed to the outside of the animal) with selected lipophilic fluorescent dyes (Hedgecock, E., *Worm Breeders Gazette* 11:56 (1989); Hedgecock, E. et al., "*Dev. Biol.* 111:185–170 " (1985)).

Accordingly, an object of the invention is to provide a quick, reliable, accurate, and inexpensive method of detecting ivermectin resistance and resistance to related compounds (avermectins, milbemycins, and related synthetic compounds) in parasitic nematodes. A specific object of the invention is to provide a procedure to detect resistance in significant parasitic nematodes including, but not limited to *Onchocerca volvulus*, which is responsible for river blindness, and other *Onchocerca spp.*, *Dirofilaria immitis* (heartworm), *Ascaris suum*, *Haemonchus contortus*, *Trichostrongylus colubriformis*, and *Ostertagia circumcincta* (parasites of sheep).

A specific object of the invention is the diagnosis of resistance by analysis of defects in the membranes of the sensory neurons that are exposed to the outside surface of the nematode in the sensillum of significant parasitic nematodes.

A further object of the invention is to provide a method for diagnosing resistance by the use of lipophilic dyes that stain the membranes of sensory neurons on the outside surface of the wild-type nematode, but not the resistant nematode. Either fluorescent or visible lipophilic dyes are used. A suitable dye is one that can be easily detected on the surface of the wild-type nematode (by means of the intercalation and diffusion of the dye in the membranes of the outer sensory neurons in the sensillum). A further specific object of the invention is to provide a diagnostic method for detecting low-level ivermectin (and related compound) resistance.

The method is directed to incubating the membranes with the lipophilic dye. The whole animal or parts thereof may be used. The resulting levels of dye are then compared to control levels in wild-type or other mutant membranes.

DETAILED DESCRIPTION OF THE PREFERRED EMBODIMENTS

The present invention is based on the inventors' realizations that a powerful diagnostic tool could be provided for the rapid, inexpensive, and accurate detection of low-level ivermectin resistance and resistance to related compounds of parasitic nematodes in the field. The inventors' observations of a strong positive correlation between certain defects in chemosensory function in *C. elegans* and the presence of low-level ivermectin resistance combined with the previous reports that these chemosensory mutations prevented the staining of sensory neurons in the membranes normally exposed to the outside of the animal provided the diagnostic method.

Accordingly, in a broad embodiment of the invention, the diagnosis of avermectin/milbemycin and related compound resistance is provided by analysis of defects in the sensillum of parasitic nematodes. The defects are such that the binding of specific lipophilic dyes (and the subsequent intercalation and diffusion) to membranes of the sensory neurons in the sensillum, and particularly the neurons that are exposed on the outside of the animal, is prevented or reduced.

In further embodiments of the invention, diagnosis of resistance is effected through the use of lipophilic dyes that stain the outer sensory neurons in the sensillum of wild-type nematodes but not resistant nematodes or stain resistant nematodes at reduced levels.

In a further embodiment of the invention, the diagnosis of resistance is accomplished by the use of fluorescent lipophilic dyes that include but are not limited to FITC, DiO, and DiI.

In a further embodiment of the invention, the diagnosis of resistance is accomplished by the use of lipophilic dyes that are within the visible spectrum and thus are detectable with the naked eye. Such dyes would be known to the ordinary skilled artisan.

In preferred embodiments of the invention, the method is used to detect resistance of parasitic nematodes to ivermectin. In further embodiments of the invention, however, the method is used to detect resistance to any of the related compounds of ivermectin. These are broadly the avermectins and milbemycins. These include, but are not limited to abamectin, doramectin, moxidectin, milbemycin B-41D, milbemycin $A_1$.

Accordingly, in the methods of the present invention, the sensillum of the parasitic nematode with the sensory neurons on the outside of the surface of the animal is incubated in the presence of the specific dye. The entire animal may be incubated, or parts thereof containing the sensillum. The amount of dye in the membrane of the sensory neuron of the incubated sensillum may then be quantitated relative to an amount found in a control animal, for example, wild-type. The binding of the relevant dyes to the membranes of the sensory neurons in the sensillum can be achieved by standard methods known to the ordinary skilled artisan (Hedgecock, and Hedgecock, et al., supra).

In further embodiments of the invention, the diagnosis of resistance is provided by staining the sensory neurons with the fluorescent lipophilic dyes DiO, FITC, or DiI. In further preferred embodiments of the invention, the diagnosis of resistance is performed in the parasitic nematodes including, but not limited to *Onchocerca volvulus* and other *Onchocerca spp.*, *Dirofilaria immitis*, *Ascaris suum*, *Haemonchus contortus*, *Trichostrongylus colubriformis*, *Ostertagia circumcincta*, *Toxacara canis*, *Toxacara cati*, *Ascaris lumbricoides*, *Brugia malayi*, *Wuchereria bancrofti*, and *Meloidogyne spp.*

Having now described the invention in general terms, the same will be further described by reference to certain specific examples that are provided herein for the purposes of explanation only and are not intended to be limiting unless otherwise specified.

Definitions

By "resistance" is meant the continued function and viability in concentrations of the specific drug which would render the wild-type animal inviable or dysfunctional.

By "membranes of sensory neurons on the outside or outer surface of the animal" is intended those sensory neurons that are found in sensillum, which neurons are actually exposed to the outer surface of the nematode such that the binding of the lipophilic dye of relevance to the invention to the membrane of the sensory neuron and resulting in intercalation and diffusion of the dye in the membrane, is actually visible on the surface of the animal with the naked eye or by means of fluorescent detection.

By "FITC" is intended fluorescein isothiocyanate.

By "DiO" is intended 3,3'-dioctadecyl-oxacarbocyanine perchlorate.

By "DiI" is intended 1,1'-dioctadecyl-3,3,3'-tetramethyl indocarbocyanine perchlorate.

By "parasiticide" is intended an agent that kills viral, bacterial, fungal, or animal parasites.

By "endectocide" is intended an agent that kills endo- and ectoparasites.

By "drug resistance" is intended a state in which there is a change in the gene frequency of a population, such change being produced by drug selection and characterized in that more drug is required to exact some specific effect than was required prior to selection.

By "side-resistance" is intended a state in which a drug-selected population has a gene(s) coding for a mechanism that defeats the toxicity of drugs within a mode of action family.

By "cross-resistance" is intended a state in which a drug-selected population has a gene(s) coding for a mechanism that defeats the toxicity of drugs from different mode of action families.

By "multiple resistance" is intended a state in which a population has been selected independently by drugs from different mode of action families to produce different but concurrent mechanisms of erosion, as used herein, or it is sometimes used as a synonym of cross-resistance.

EXAMPLE 1

Ivermectin Resistance in Free-Living Nematodes

Low-level ivermectin resistance in four non-*C. elegans* species of free-living nematodes occurs in frequencies similar to those observed in *C. elegans*.

Previous research has identified many genes that can mutate to confer ivermectin resistance in *Caehorhabditis elegans*. As a further step toward identifying those avermectins resistant (avr) genes whose homologues are likely to be responsible for resistance in economically or medically significant parasitic nematodes, ivermectin resistance in other free-living nematodes has been investigated.

Such investigation has determined that in as *C. elegans*, low-level (5–15×) resistance to ivermectin is common both in the hermaphroditic species, *C. briggsae*, as well as in the diecious species, *C. remanei*, *C. vulgaris*, *Pellioditis pellio* and *Panagrellus redivivus*. As expected, high-level (>100×) resistance is much rarer. So far, isolation of high-level resistance strains of the diecious species (>$10^7$ mutagenized genomes screened) has not been accomplished. The incidence of high-level resistance in *C. briggsae* is 1 in 5,000 mutagenized genomes, significantly different than that observed in *C. elegans* (1 in 10 million genomes). This resistance frequency observed in *C. briggsae*, suggests that single mutations can confer high-level resistance in this species. High-level resistance in *C. elegans* has been shown to require two mutations. In addition, all high-level resistant strains of *C. briggsae* are uncoordinated in the presence of ivermectin whereas some *C. elegans* high-level resistant strains have no behavioral defect in the presence of drug.

EXAMPLE 2

Amphid Function, Chemotaxis and Ivermectin Resistance

Some mutations that confer defects in chemosensory function (and had been previously identified as mutants of che, osm, or daf genes) also confer low-level ivermectin resistance. Of most significance, there is a positive correlation between the che, osm, or daf mutations that confer ivermectin resistance and those mutations which have previously been reported to lack the staining of sensory neurons whose membranes are normally exposed to the outside of the animal.

While studying the genetics of ivermectin resistance, it was noticed that worms showed poor orientation on drug, suggesting that ivermectin interferes with chemoreception or chemotaxis. To investigate this further, a small selection of known chemotaxis-defective strains, which also had specific neurotransmitter defects, were subjected to testing. Those which had defective amphids were resistant, and there was no correlation with any particular neurotransmitter deficiency. Further testing of a more complete collection of che, osm, mec and daf mutants with amphid defects showed that there is a relationship between amphid function (as assayed by FITC staining) and sensitivity to ivermectin: all strains with amphid defects were able to grow in the presence of 5 ng/ml of ivermectin. A small selection of avr mutants were tested for their ability to form dauer larvae following starvation on NGM at 25° C. At least some were found to be dauer defective.

EXAMPLE 3

Staining of Low-Level Ivermectin Resistant Mutants

Forty-eight low-level ivermectin-resistant mutants of *C. elegans* were tested for staining of sensory neurons with DiO. Forty-seven of these mutants displayed a readily detected difference from wild-type. In thirty-nine strains, no staining was observed, and in eight strains, partial staining was observed. Further, a low-level ivermectin resistant strain of *C. vulgaris* failed to stain with DiO.

EXAMPLE 4

Staining of Free-Living Species of Nematodes

Wild-type strains of 12 non-*C. elegans* free-living species of nematodes were stained with DiO and sensory neuron staining was observed. It was found that only one of these 12 additional species did not stain.

Having now fully described this invention, it will be understood by those with skill in the art that the same may be performed within a wide and equivalent range of conditions, parameters, and the like, without affecting the spirit or scope of the invention or of any embodiment thereof.

What is claimed is:

1. A method for diagnosing avermectin or milbemycin resistance in a parasitic nematode, said nematode having sensillum comprising sensory neurons, said method comprising (1) exposing said sensillum to a means for detecting a defect in said sensillum, said defect preventing intercalation and diffusion of a lipophilic dye into membranes of sensory neurons in said sensillum, (2) detecting the presence of said defect, and (3) diagnosing avermectin or milbemycin resistance by correlating the presence of said defect with avermectin or milbemycin resistance.

2. A method for diagnosing avermectin or milbemycin resistance in a parasitic nematode, said nematode having sensillum comprising sensory neurons, said method comprising (1) incubating said sensory neurons of said sensillum of said nematode, which sensory neurons are normally exposed to the outer surface of said nematode, with a lipophilic dye capable of staining said sensory neurons in a wild-type nematode, (2) observing said sensory neurons after incubation with said dye, and (3) diagnosing avermectin or milbemycin resistance by correlating the absence of staining of said sensory neurons with said dye with avermectin or milbemycin resistance.

3. The method of either of claims 1 or 2 wherein said nematode is ivermectin-resistant.

4. The method of claim 3 wherein said dye is selected from the group consisting of a fluorescent dye and a visible dye.

5. The method of claim 4 wherein said dye is selected from the group consisting of fluorescein isothiocyanate 3,3'-dioctadecyl-oxacarbocyanine perchlorate, and 1,1'-dioctadecyl-3,3,3'-tetramethyl indocarbocyanine perchlorate.

6. The method of either of claims 1 or 2, wherein said parasitic nematode is selected from the group consisting of *Haemonchus contortus, Trichostrongylus colubriformis, Ascaris suum, Ostertagia circumcincta, Toxacara canis, Toxacara cati, Dirofilaria immitis, Ascaris lumbricoides, Brugia malayi, Wuchereria bancrofti, Onchocerca volvulus* and Meloidogyne spp.

7. The method of either of claims 1 or 2, wherein said nematode is doramectin-resistant.

8. The method of either of claims 1 or 2, wherein said nematode is moxidectin-resistant.

9. The method of claim 2 wherein said dye is selected from the group consisting of a fluorescent dye and a visible dye.

10. The method of claim 9 wherein said dye is selected from the group consisting of florescein isothiocyanate 3,3'-dioctadecyl-oxacarbocyanine perchlorate, and 1,1'-dioctadecyl-3,3,3'-tetramethyl indocarbocyanine perchlorate.

* * * * *